United States Patent
Song

[11] Patent Number: 5,330,500
[45] Date of Patent: Jul. 19, 1994

[54] SELF-EXPANDING ENDOVASCULAR STENT WITH SILICONE COATING

[76] Inventor: Ho Y. Song, 803, Keosung Kosok-mansion, 1168-2, Jinbuk-dong, Cheonju-si, Cheonrabuk-do, Rep. of Korea, 560-160

[21] Appl. No.: 861,785
[22] PCT Filed: Oct. 17, 1991
[86] PCT No.: PCT/KR91/00023
§ 371 Date: Jun. 15, 1992
§ 102(e) Date: Jun. 15, 1992
[87] PCT Pub. No.: WO92/06734
PCT Pub. Date: Apr. 30, 1992
[51] Int. Cl.⁵ .............................. A61M 29/00
[52] U.S. Cl. ........................ 606/198; 623/1
[58] Field of Search ............ 623/1, 12; 606/151, 606/153, 191, 195, 198

[56] References Cited

U.S. PATENT DOCUMENTS

| | | | |
|---|---|---|---|
| 4,580,568 | 4/1986 | Gianturco | 128/345 |
| 4,596,577 | 6/1986 | Sato | 623/1 |
| 4,733,665 | 3/1988 | Palmaz | 606/191 |
| 4,886,062 | 12/1989 | Witkor | 606/194 |
| 5,019,090 | 5/1991 | Pinchuk | 623/1 |
| 5,035,706 | 7/1991 | Giantureo et al. | 606/198 |
| 5,064,435 | 11/1991 | Porter | 606/198 |
| 5,116,360 | 5/1992 | Pinchuk et al. | 623/1 |
| 5,151,105 | 9/1992 | Kwan-Gett | 606/191 |
| 5,167,614 | 12/1992 | Tessman et al. | 623/1 |
| 5,192,311 | 3/1993 | King et al. | 623/1 |

FOREIGN PATENT DOCUMENTS 1766921 8/1968 Fed. Rep. of Germany.

Primary Examiner—Jerome L. Kruter
Attorney, Agent, or Firm—Christie, Parker & Hale

[57] ABSTRACT

A radially expandable stent is useful for holding a passageway open by placing the stent into a lumen. The stent includes a cylindrical frame formed by a plurality of unit structures. Each unit structure is of a closed zig-zag configuration including an endless series of straight sections joined by bends. The plurality of unit structures are arranged end to end to form the frame. A plurality of connecting members connect the unit structures together. The outer surface of the frame is wrapped with mesh, which is preferably coated with silicone rubber.

6 Claims, 4 Drawing Sheets

SELF-EXPANDING ENDOVASCULAR STENT WITH SILICONE COATING

TECHNICAL FIELD

This invention relates to improvements of endovascular stent

BACKGROUND ART

It is desirable in various situations that means be provided for expanding a constricted vessel portion or for maintaining an open passageway through a vessel portion.

For example, these situations can be those by esophageal strictures that are caused by esophageal carcinoma or esphageal metastasis, or those by strictures that resulted from the cancer of biliary system, urinary duct system and bronchial system.

The balloon expansion has been well known method of enlarging and maintaining the passageway of esophagus in these cases; but this method should be operated repeatedly for its temporary effects, and also it has no effects on the patients of serious strictures.

As alternatives, various artificial-esophagi have been used in the cases of esophageal strictures, but since they have no constriction and relaxation, the rate of esophageal rupture is high (30–40%) in the process of inserting them into the strictural area that has been caused by the cancer, and the high mortality rate due to mediastinitis results from rupture of esophagus. In addition, the patient has a great difficulty in swallowing due to narrow inner diameter (10-12 mm) of artificial esophagus, and obstruction of artificial-esophagus occurred frequently due to food intake.

As the means of overcoming the difficulty, a device to hold the passageway enlarged using a stent was presented by U.S. Pat. No. 4,214,587. However, the device of the invention has the temporary effect in enlarging the passageway, there is still the problem that the endovascular lumen gets narrows after a long time.

To improve this disadvantages, U.S. Pat. No. 4,580,568 was offered. The stent of said invention includes a wire formed into a closed zig-zag configuration including an endless series of straight sections joined by bends. The stent is resiliently compressible into a smaller first shape wherein the straight sections are arranged side-by-side and closely adjacent one another for insertion into a larger second shape wherein said straight sections press against the walls of the passageway to maintain it open.

However, in a case that the stent of the U.S. Pat. No. 4,580,568 invention is put into use for a long time, it still has the problem that the lumen is narrowed, because the proliferated cells cover the stent thickly. There is no effect in the case of the stricture by cancer, because the cancer cells can pass through the straight sections.

DISCLOSURE OF INVENTION

In view of the foregoing, it is the main object of this invention to provide a self-expanding endovascular stent, which expands a constricted vessel portion and maintains an open passageway through a vessel portion for a long time without moving in a lumen.

It is another object of the present invention to provide a self-expanding endovascular stent, which prevents the cancer cells to penetrate into a stent.

To accomplish said purposes, this invention provides, a stent, which comprises a cylindrical frame formed by a plurality of unit structures;

said unit structures formed into a closed zig-zag configuration including an endless series of straight sections and joined by bends, and arranged face to face into a shape of multistage; connecting members, which connects said unit structures one another and a mesh, which is wrapped around an outside of said frame.

And another stent according to the present invention comprises a cylindrical frame formed by a plurality of unit structures; said unit structures formed into a closed zig-zag configuration including an endless series of straight sections, joined by bends, and arranged face to face into a shape of multistage; connecting members, which connects said unit structures one another; anti-migration members, which have the same structure with said unit structure, and placed in the ends of the upper and lower portions of said frame; and a mesh, which is wrapped around an outside of said frame.

BEST MODE FOR CARRYING OUT THE INVENTION

Figure 1:
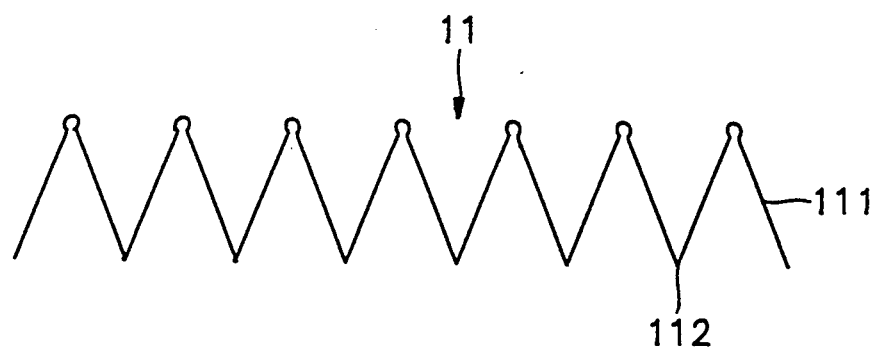
FIG. 1 is a development figure that illustrates a unit structure of a frame according to the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such applications of the principles of the invention as illustrated therein being contemplated as would normally occur of one skilled in the art to which the invention relates.

Figure 2:
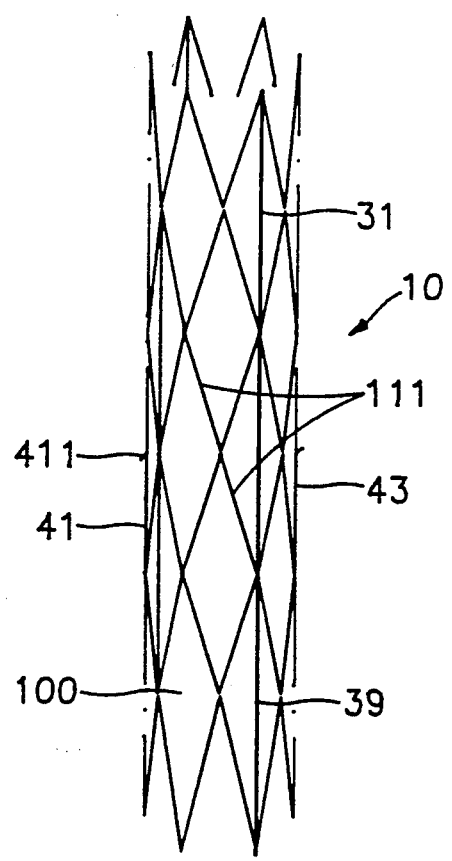
FIG. 2 is a perspective view of a first embodiment that illustrates a frame according to the present invention.
Figure 3:
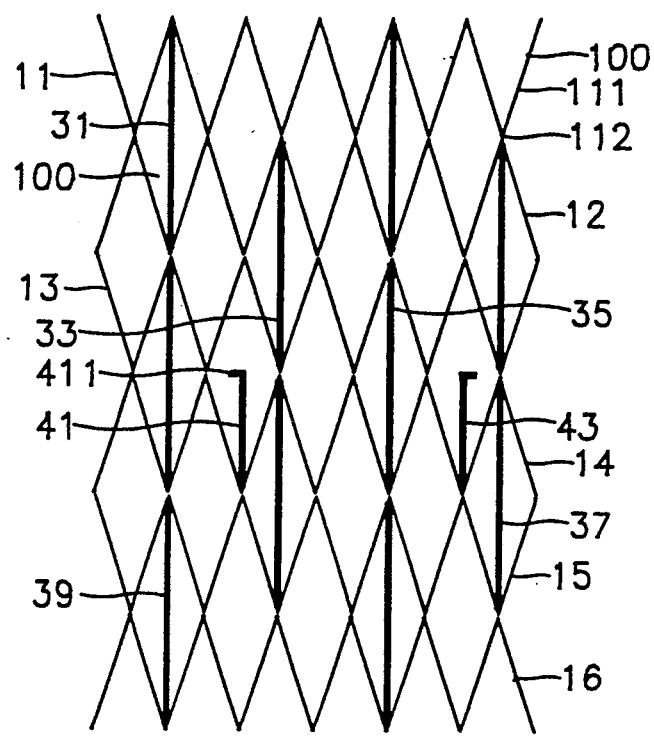
FIG. 3 is a development figure of said frame of the first embodiment of the invention.
Figure 4:
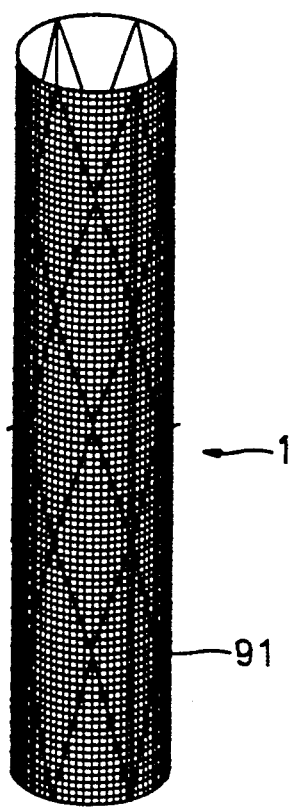
FIG. 4 is a perspective view of the first embodiment according to the invention.
Figure 5:
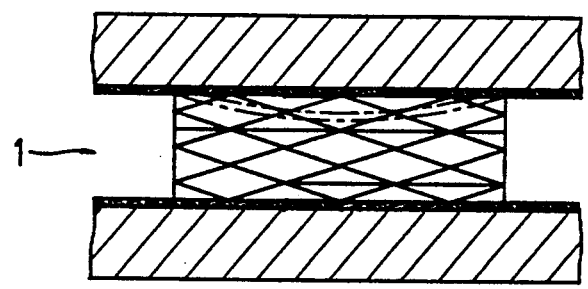
FIG. 5 is a view of showing a state that a stent of the first embodiment according to the present invention is placed and enlarged in a lumen.

FIG. 1 is a development figure that illustrates the unit structure of a frame according to the present invention; FIG. 2 is a perspective view of the first embodiment that illustrates a frame according to the present invention; FIG. 3 is a development figure of said frame of FIG. 2.

A frame 10 of the first embodiment comprises a reasonable number of unit structures 11 as shown in FIG. 1. The unit structure 11 is constructed of a wire, and the wire is preferably made of stainless steel. The unit structure 11 is formed into a closed zig-zag configuration, thereby forming a series of straight sections 111 and bends 112 as shown in FIG. 1. Both ends of the wire are joined to each other by welding, thereby forming an endless series of straight sections joined by bends.

Frame 10 is constructed in a way that a plurality of said unit structures 11 closely similar to each other and bends corresponding to each of the unit structures are arranged face to face into a shape of a multistage. At this time, every unit structure is connected in tandem by a reasonable number of connecting members 31, 33, 35, 37. These connecting members are joined appropriately between the bends of appointed unit structure such that they prevent each unit structure from being separated. The most preferable joint position of the connecting members is to be placed diagonally, regarding the connecting member 31 as a fiducial point as shown in FIG. 3. Namely, it is preferable to have a construction 31, 33, 35, and 37 as can be seen in FIG. 3. Also, the connecting members are not connected with every other bend and the frame 10 wherein an appropriate number of connecting members in one unit structure 11 i.e. ten connecting members in the first embodiment of FIG. 3 are connected to each other, has a plurality of diamond-like spaces 100. The number of the unit structure or the connecting members do not have a special meaning, and may be varied according to a state of a patient and/or convenience of production.

The space areas receive the straight section 111 when the straight section 111 is shrinked, making an elasticity variation with the bend 112.

A completed frame 10 has anti-migration members 41, 43 for preventing migration of a stent in a lumen that are equipped with barbs that jut outside. The anti-migration members 41, 43 are properly arranged and connected with the bends which the connecting members 31, 33, 35, 37 are not connected. Therefore, the stent 1 of the present invention does not move in a lumen.

All the unit structures, the connecting members, and the anti-migration members are made of the same material like stainless steel, preferably are gilt.

The frame 10 is wrapped in a mesh 91, and upper and lower hem of the mesh 91 are folded towards inside, and both hems become respectively adhesive whereby a wire of the unit structure 11 is not exposed. It is preferable that the mesh is made of nylon and the nylon mesh is coated with silicon rubber.

The method of 587 U.S. patent or a method using a catheter in which the stent of the invention being compressed may be used in order to place the stent of the present invention at a position, namely a diseased part in a lumen.

The stent is fixed on inner walls of the lumen with the barb 411 of the anti-migration member, and though the stent is used for a long time, it does not migrate, and in addition thereto, pain that a patient may feel can be relieved, compared with conventional stent, because an outer wall of the stent 1 is wrapped with mesh 91. Furthermore, the silicon rubber coating on the mesh 91 can prevent that cancer cell and the like penetrate into the inside of the stent.

As a result of experimenting the first embodiment of this invention on patients with gastric cancer or esophageal cancer, following effects are obtained.

A. A patient with gastric cancer and esophageal spreading of gastric cancer came to Hospital of Cheon Buk Medical College on July, 1989. The symptoms of the patient were improved after six times medicine of anti-cancer. But the patent revisited to the medical college for an appearance of a dysphagia.

On Jan. 8, 1990, an obstructed area of distal portion of esophagus due to spreading of gastric cancer, was enlarged with an esophageal balloon of 20 mm in diameter and 8 cm in length, and then a stent of 20 mm in external diameter and 8 cm in length was intubated into a strictural area of esophagus through a sheath of 10 mm.

After operation, the patient was able to eat liquid food and solid food, and in esophagogram performed in seven days after operation, a balium passed well through esophagus without any undercurrent or obstruction, and specific complications such as the migration of the stent or the rupture of the esophagus, did not occur.

After that, the patient left the hospital, and died of a generalized metastasis of gastric cancer on April, 1990. However, there was no problem with the function of the stent until just before the patient's death.

B. A patient with gastric cancer and esophageal metastasis came to Hospital of Cheon Buk Medical College owing to dysphagia on Mar. 13, 1990.

After an obstructed portion of esophagus was enlarged with an esphageal balloon of 20 mm in diameter and 8 cm in length, a stent of 20 mm in external diameter and 10 cm in length was intubated into the distal portion of esophagus through the sheath of 10 mm in external diameter.

As a result of the operation, the patient was not able to eat even water, but after the stent was intubated into his lumen, the patient was able to taking the liquid food and solid food, and a balium passed well through without any undercurrent or obstruction in esophagogram performed in seven days after the operation. When endoscope is performed on Mar. 27, 1990, the endoscope of 10 mm in external diameter was passed through without any difficulty.

And in following up examination of esophagogram performed on Aug. 10, 1990, any specific complications like the moving or the obstruction of the stent did not occur, and in addition, the patient was able to eat the liquid food and solid food.

C. A patient with the esophageal carcinoma was hospitalized in the Hospital of Cheon Buk Medical College, and took radiotherapy and medicated anti-cancer medicine five times, and then symptoms were improved, but the patient revisited to the hospital due to the dysphagia.

After the obstructed area of the esophagus was dilated with the esophageal balloon of 20 mm in diameter and 8 cm in length, the stent of 20 mm in external diameter and 12 cm in length was intubated into the obstructed area of the esophagus through the 10 mm sheath.

As a result of the treatment, the patient was able to eat liquid food and solid food, balium passed well through without any undercurrent or obstruction in esophagogram, and any complication like the migration of the stent or the rupture of the esophagus did not occur.

As medical appliance of the present invention is proved by the experiment on the above, since the expansile force of the stent that is intubated into an appointed area and is kept, is excellent, the outstanding effects that keep the stricture of passageway enlarged can be obtained.

The construction of the first embodiment as mentioned above is expected of preventing the migration of the stent, but since the distal ends of the anti-migration members 41, 43 have barbs that jut out externally, the possibility cannot be excluded that the barbs cause a patient to feel pain and lumen perforation, and when the stent is artificially transferred to set the position of the stent to rights, the lumen wall can be hurt.

Figure 6:
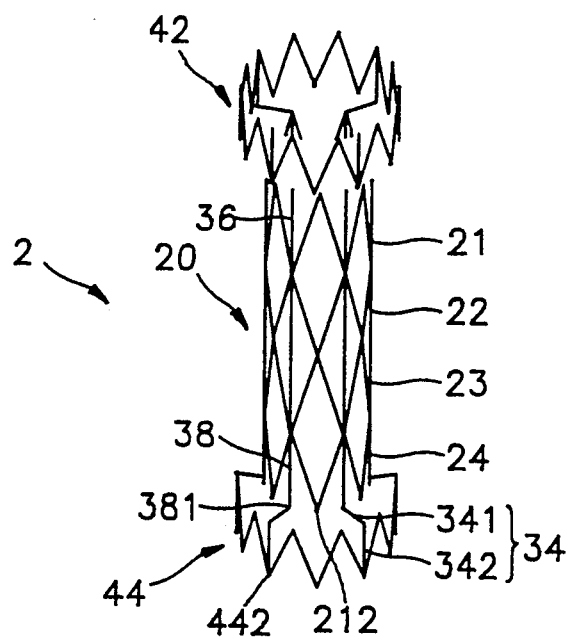
FIG. 6 is a perspective view of a second embodiment according to the present invention that illustrates a frame.

FIG. 6 is a perspective view of a second embodiment of the present invention, and shows that a plurality of unit structures 21, 22, 23, 24 are linker, being expanding. The unit structures 21, 22, 23, 24 are identical with the unit structures of the first embodiment.

According to the second embodiment of this invention, the stent comprises the frame 20 formed by a plurality of connected unit structures 21, 22, 23, 24, and anti-migration members 42 and 44 placed in lower and upper portions of the frame 20. The frame 20 without anti-migration members 42 and 44 is almost same with the frame of the first embodiment of this invention except for the numbers of the unit structures and the length of connecting members 36, 38. The numbers of unit structures have no meaning in this invention. And the length of connecting members 36, 38 in the ends of the upper and lower portions of the frame 20 is a half of the length of the connecting members 31, 39 of the first embodiment of this invention.

The both side sections of the unit structures 21, 24 are connected with the anti-migration members 42 and 44 through the second connecting members 32, 34.

Anti-migration members 42 and 44 placed in the ends of the upper and lower portions of the frame 20 have the same structures with the unit structures 21, 22, 23, 24. But the anti-migration members 42 and 44 are formed to be larger than the frame 20 in diameter. To connect the frame 20, and the anti-migration members 42 and 44, that are different from each other in diameter, is available through the second connecting members 32, 34. The second connecting member 34 connects a bend 381 or the end 381 of the connecting member 38 with a bend 442 of the anti-migration member 44. This connection is performed by welding.

Since the diameter of the anti-migration members 42 and 44 depends on the length of horizontal parts 321, 341 of the second connecting members 32, 34, it is important to determine the length thereof. Expansile parts 322, 342, expanded from the horizontal parts 321, 341 and bended vertically.

It is omitted in FIG. 6 that a mesh is wrapped around the outside of the frame 20.

The stent 2 formed as mentioned above keeps expanded unless force is given thereto. In order to place the stent within an esophagus, a given introducing assembly such as an introducing tube, an esophageal balloon and a pusher catheter are pushed into a stricture in a compressed state.

As the introducing tube is removed over the pusher catheter, the compressed stent is automatically passed through and expanded.

Figure 7:
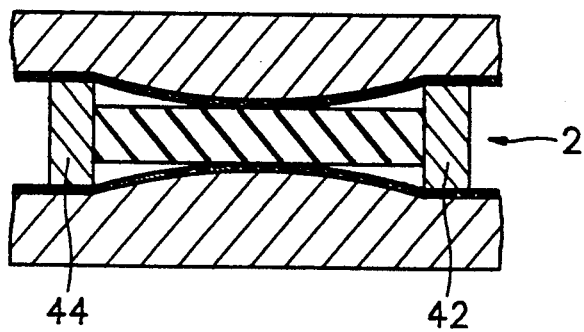
FIG. 7 is a view of showing a state that a stent of the second embodiment of the present invention is placed and enlarged in a lumen.
Figure 8:
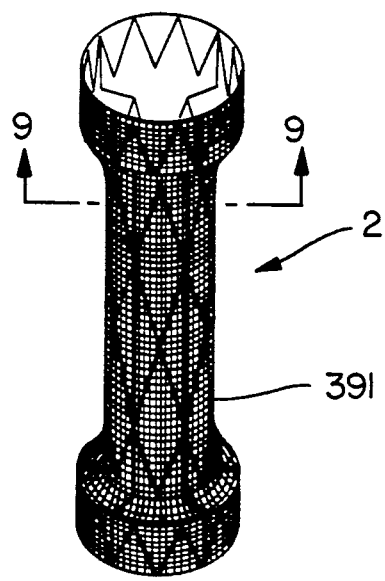
FIG. 8 is a perspective view of a second embodiment according to the invention.
Figure 9:
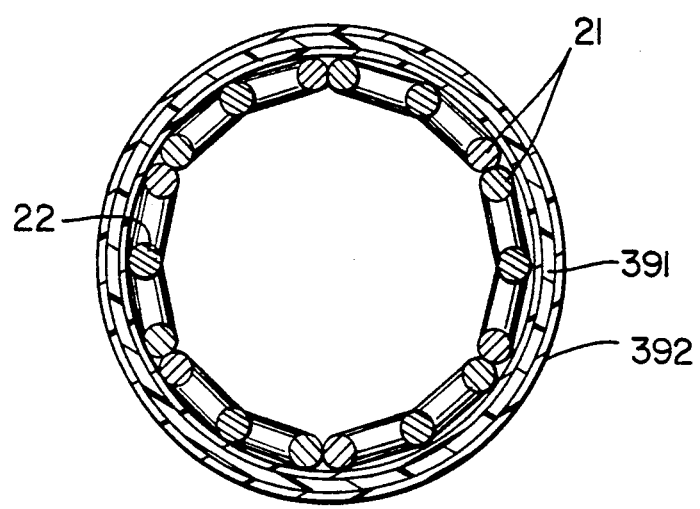
FIG. 9 is a sectional view taken along line 9—9 of FIG. 8.

FIG. 7 is an explanatory view of the state that the stent 2 placed within a lumen is radially expanded to stick to the lumen.

A stent that can be used for patients with esophageal carcinoma is described above, and if a stent was formed to be cylindrical between 8 mm to 10 mm in diameter, other applications of the stent are in the biliary, bronchial and urinary systems.

I claim:

1. A self-expanding stent comprising:
   a cylindrical main frame of a first diameter and comprising a plurality of unit structures, each unit structure formed in an endless zig-zag configuration;
   a plurality of connecting members for connecting the unit structures to one another while allowing expansion and contraction of the main frame;
   an anti-migration frame fastened to the main frame for preventing the stent from migrating, the anti-migration frame having the same structure as the main frame and a second diameter larger than the first diameter of the main frame; and
   a mesh wrapped around an outer surface formed by the main frame and the anti-migration frame,
   wherein the stent further comprises a coating of silicone rubber over the mesh.

2. The stent of claim 1 wherein the anti-migration frame is a first anti-migration frame fastened to a first end of the main frame, the stent further comprising a second anti-migration frame fastened to a second end of the main frame opposite the first end.

3. The stent of claim 2 wherein the main frame and anti-migration frames are made of stainless steel.

4. The stent of claim 3 wherein the main frame and anti-migration frame are gilt.

5. The stent of claim 2 wherein the mesh is nylon.

6. A self-expanding stent comprising:
   a cylindrical main frame of a first diameter comprising a plurality of unit structures and having an axial direction, each of the unit structures comprising a unitary member formed into an endless zig-zag configuration, and having an axial direction which coincides with the axial direction of the cylindrical main frame;
   a plurality of connecting members for connecting the unit structures to one another with the unit structures abutting and being stacked in an axial direction, and for allowing radial expansion and contraction of the main frame;
   an anti-migration frame fastened to the main frame for preventing the stent from migrating, the anti-migration frame having the same structure as the main frame and a second diameter larger than the first diameter of the main frame; and
   a mesh wrapped around an outer surface formed by the main frame and the anti-migration members,
   wherein the stent further comprises a coating of silicone rubber over the mesh.

* * * * *